(12) United States Patent
Li et al.

(10) Patent No.: US 8,841,419 B2
(45) Date of Patent: Sep. 23, 2014

(54) HYBRIDOMA CELL LINE 10G4 AND A MONOCLONAL ANTIBODY AGAINST THE TOTAL OF AFLATOXIN B1, B2, G1 AND G2

(71) Applicant: Oil Crops Research Institute Of Chinese Academy Of Agricultural Sciences, Hubei (CN)

(72) Inventors: Peiwu Li, Hubei (CN); Xin Li, Hubei (CN); Qi Zhang, Hubei (CN); Xiaoxia Ding, Hubei (CN); Wen Zhang, Hubei (CN); Ran Li, Hubei (CN); Zhaowei Zhang, Hubei (CN)

(73) Assignee: Oilcrops Research Institute of Chinese Academy of Agriculture Sciences, Wuhan, Hubei (CN)

( * ) Notice: Subject to any disclaimer, the term of this patent is extended or adjusted under 35 U.S.C. 154(b) by 0 days.

(21) Appl. No.: 13/984,231

(22) PCT Filed: Jan. 17, 2013

(86) PCT No.: PCT/CN2013/070612
§ 371 (c)(1),
(2), (4) Date: Aug. 7, 2013

(87) PCT Pub. No.: WO2013/155882
PCT Pub. Date: Oct. 24, 2013

(65) Prior Publication Data
US 2014/0057294 A1 Feb. 27, 2014

(30) Foreign Application Priority Data

Apr. 20, 2012 (CN) .......................... 2012 1 0117612

(51) Int. Cl.
*C07K 16/00* (2006.01)
*C07K 16/14* (2006.01)
*G01N 33/577* (2006.01)

(52) U.S. Cl.
CPC .............. *C07K 16/14* (2013.01); *G01N 33/577* (2013.01)
USPC .................................... 530/387.1; 530/388.5

(58) Field of Classification Search
None
See application file for complete search history.

(56) References Cited

FOREIGN PATENT DOCUMENTS

| CN | 101993855 A | 3/2011 |
|---|---|---|
| CN | 102220286 A | 10/2011 |
| CN | 102747042 A | 10/2012 |
| EP | 2090590 A | 8/2009 |
| JP | 04360695 A | 12/1992 |

OTHER PUBLICATIONS

State Intellectual Property Office of the People's Republic of China, "Office Action", China, Jan. 17, 2013.
State Intellectual Property Office of the People's Republic of China, "Notice of Allowance", China, Feb. 18, 2013.
State Intellectual Property Office of the People's Republic of China, "Search Report", China, Nov. 6, 2012.
State Intellectual Property Office of the People's Republic of China, "International Search Report", China, Apr. 18, 2013.
Jiang Tao et al., "Development of Hybridoma Cell Line Excreting Monoclonal Antibody Against Total Aflatoxins", China Prev Med, Feb. 2007, vol. 8, No. 1, p. 16-19, Abstract Only.
Ji Rong et al., "Development of ELISA—kit of quantitative analysis for Aflatoxins", China J Public Health, Mar. 2007, vol. 23, No. 3, p. 331-333, Abstract Only.
Xiao Zhi et al., "Production and characteristics of specialised monoclonal antibodies against aflatoxin B1", Chinese journal of oil crop sciences, Feb. 2011, p. 66-70, Abstract Only.

*Primary Examiner* — Shafiqul Haq
*Assistant Examiner* — Carmencita M Belei
(74) *Attorney, Agent, or Firm* — Tim Tingkang Xia, Esq.; Morris, Manning & Martin, LLP

(57) ABSTRACT

Hybridoma cell line 10G4 and monoclonal antibody against total aflatoxins produced by the hybridoma cell line 10G4. The hybridoma cell line 10G4 is used to produce the monoclonal antibody that binds specifically total aflatoxin B1, B2, G1 and G2. The titer of the mouse ascites antibody produced by the 10G4 treated mouse is determined through non-competitive enzyme-linked immunosorbent assay and the titer can reach up to $5.12 \times 10^5$. The monoclonal antibody against total aflatoxin B1, B2, G1 and G2 are used for better identification of aflatoxin B1, B2, G1 and G2 with good consistency. The 50% inhibitory concentrations ($IC_{50}$) of the antibody against aflatoxin B1, B2, G1 and G2 are 2.09 ng/mL, 2.23 ng/mL, 2.19 ng/mL and 3.21 ng/mL respectively. The range of cross reaction rate for aflatoxin B1, B2, G1 and G2 is about 65.2%-100%. The antibody is used for quantitative measurement of total aflatoxin B1, B2, G1 and G2.

3 Claims, No Drawings

HYBRIDOMA CELL LINE 10G4 AND A MONOCLONAL ANTIBODY AGAINST THE TOTAL OF AFLATOXIN B1, B2, G1 AND G2

CROSS-REFERENCE TO RELATED APPLICATIONS

This application is a 371 of PCT/CN2013/070612, filed Jan. 17, 2013, which claims the benefit of foreign application China 201210117612.X, filed Apr. 20, 2012, the contents of each of which are incorporated herein by reference.

FIELD OF THE INVENTION

The present invention relates to a hybridoma cell line 10G4 and a monoclonal antibody produced by the same that is capable of recognizing total aflatoxins.

BACKGROUND OF THE INVENTION

Aflatoxins, natural compounds toxic to human beings and animals, are the secondary metabolites secreted by *Aspergillus flavus* and *Aspergillus parasiticus*. A variety of aflatoxins exist in the world and more than 20 kinds have been identified. Aflatoxins are characterized by wide pollution, strong toxicity and severe harm etc. Therefore, at least 70 countries in the world have established maximum residue limit with regard to aflatoxins contained in agriculture products and foods. Many countries have even established maximum residue limit with regard to the total amount of those main aflatoxins such as B1, B2, G1 and G2, so the total aflatoxin analysis is very important.

The current aflatoxin assay methods include thin layer chromatography (TLC), precision instrumental analysis and immunoassay. The TLC method is the most popular for testing aflatoxins since it can be performed in general labs and no special instruments are required. However, a lot of reagents are needed for the TLC assay, the operation is complicated, and other components are liable to interfere with the test result, causing poor accuracy, uncertain dosing and harm to operators and the ambient environment, which makes it unsuitable for quick on-site inspection. The precision instrumental analysis includes fluorescence spectrophotometry and high performance liquid chromatography (HPLC) characterized by high sensitivity and accuracy. However it is also unsuitable for quick inspection considering the expensive instruments, high purity requirement for aflatoxin samples, complicated and time consuming sample pre-processing and strict testing environment requirements. The immunoassay technology developed in recent years can help to avoid the shortcomings of the former two methods since it is characterized by good specificity, high sensitivity, simple pre-processing, low cost, less harm to operators and the ambient environment, and is suitable for on-site and batch inspection etc.

The immunoassay is adopted for qualitative and quantitative detection of ultra-micro residues based on the specific reaction of antigens and antibodies as well as the biological, physical or chemical magnification of antigen (or antibody) markers. For any immunoassay techniques with respect to total aflatoxin analysis, the antibody against total aflatoxins B1, B2, G1 and G2 are required. In fact, many reports regarding development of antibodies for anti-aflatoxins have been published worldwide. Further, all-purpose antibodies (polyclonal antibodies) against aflatoxins have also been reported. Moreover, some scientists have established total aflatoxin assay for aflatoxins based on the all-purpose anti-aflatoxin antibody. The all-purpose anti-aflatoxin antibody mainly features a strong, specific binding reaction with different aflatoxins and can be used for establishing immunoassay for any of the different aflatoxins. While the antibodies against total aflatoxin B1, B2, G1 and G2 feature not only strong specific binding reactions with different aflatoxins, but also, particularly, stronger sensitivity consistency with regard to the immunoassay for each aflatoxin. The all-purpose antibody mentioned in current reports published both domestically and abroad for anti-aflatoxins shows high versatility, but as for each separate aflatoxin, the sensitivity consistency of the assay is poor. Thus, the all-purpose antibody mentioned in these reports is not suitable for establishing the total aflatoxin assay for aflatoxins B1, B2, G1 and G2. Even if method of total aflatoxin assay is established based on those all-purpose antibody, the quantitative accuracy will be poor. Therefore, the development of antibodies against total aflatoxin B1, B2, G1 and G2 is very important for quick quantitative immunoassay of the total amount of aflatoxin B1, B2, G1 and G2.

SUMMARY OF THE INVENTION

In one aspect, the present application is directed to a hybridoma cell line 10G4 and a monoclonal antibody produced by the hybridoma cell line 10G4. The monoclonal antibody specifically recognizes total aflatoxin B1, B2, G1 and G2.

In one embodiment, the hybridoma cell line 10G4 was deposited at the China Center for Type Culture Collection (CCTCC), Wuhan University, Wuhan, China on Jul. 13, 2010 with the accession number of CCTCC No. C201016. The scientific name of the hybridoma cell line 10G4 is "Mouse hybridoma 10G4." The hybridoma cell line 10G4 includes gene sequence as shown in SEQ ID NO.1 of the Sequence Listing that corresponding to the heavy chain variable (VH) region of the produced monoclonal antibody. The hybridoma cell line 10G4 also includes the gene sequence of as shown in SEQ ID NO.2 of the Sequence Listing that corresponding to the light chain variable (VL) region of the produced monoclonal antibody. The produced monoclonal antibody is against total aflatoxin B1, B2, G1 and G2.

In another embodiment, the monoclonal antibody against total aflatoxin B1, B2, G1 and G2 is secreted by the hybridoma cell line 10G4 deposited in the China Center for Type Culture Collection (CCTCC) with the accession number of CCTCC NO. C201016. VH region of the monoclonal antibody contains the amino acid sequence as shown in SEQ ID NO.3 of the Sequence Listing and VL region of the monoclonal antibody contains the amino acid sequence as shown in SEQ ID NO: 4 of the Sequence Listing.

In certain embodiments, the hybridoma cell line 10G4 is obtained through a two-step selection method detailed as follows. The BALB/c mouse is immunized with complete aflatoxin antigen AFB1-BSA 4-6 times, and then is booster immunized the last time using twice the immunizing dose of the previous immunization. Next, cell fusion is conducted after three days. The fusion cells are selected by a two-step enzyme-linked immunosorbent assay (ELISA). Step one, selecting positive wells which are against aflatoxin but not against carrier protein BSA through indirect ELISA. Step two, testing culture solution of the positive wells selected via step one through indirect competitive inhibition ELISA. In step two, aflatoxin G2 can be used as the competition source—because the all-purpose antibody against aflatoxins reported worldwide shows the lowest cross reacting rate against aflatoxin G2 (<50%). The cloning is carried out through a limiting dilution method after the wells with high light absorption value and sensitivity are selected. The same two-step selection is performed after about 10 days from cloning. The cloning process is repeated 2-3 times, and the hybridoma cell line 10G4 is finally obtained.

The monoclonal antibody against total aflatoxin B1, B2, G1 and G2 can be used for measurement of total aflatoxin B1, B2, G1 and G2.

In certain embodiments, monoclonal antibody against total aflatoxin B1, B2, G1 and G2 are prepared as follows. A BALB/c mouse is pretreated by Freund's incomplete adjuvant. Then the treated BALB/c mouse is injected with the obtained hybridoma cell line 10G4. The ascites of the mouse is collected, and the monoclonal antibody against total aflatoxin B1, B2, G1 and G2 are obtained after purification.

In one embodiment, the purification is carried out through the caprylic acid-ammonium sulfate (CA-AS) precipitation method detailed as follows. The mouse ascites is filtered with a piece of double-layer filter paper. The filtrate is centrifuged at 12000 r/min under 4° C. for more than 15 minutes (min), and the supernatant is pipetted. The supernatant of the ascites is mixed with four times volume of acetate buffer solution, and n-Caprylic acid is added slowly while stirring. The volume of n-Caprylic acid needed for each milliliter (mL) of ascites is about 30~35 μL. The solution is mixed at room temperature for 30~60 min and then kept at 4° C. for more than 2 hours (h). Then the above solution is centrifuged at 12000 r/min under 4° C. for more than 30 min. The precipitate is discarded and the obtained supernatant is filtered with a piece of double-layer filter paper. 0.1 mol/L (M), pH 7.4 phosphate buffer solution (1/10 of the volume of the filtrate) is added to the filtrate, and the pH value of the mixture is adjusted to 7.4 with 2 M sodium hydroxide solution and precooled to about 4° C. Ammonium sulfate is added slowly to the mixture until the final concentration of ammonium sulfate reached 0.277 g/mL. The solution is kept for more than 2 h at 4° C. and then centrifuged at 12000 r/min under 4° C. for more than 30 minutes. The supernatant is discarded and the obtained precipitate is re-suspended with 0.01 M phosphate buffer solution that is 1/10 of the volume of the original ascites. The re-suspended solution is put into a dialysis bag for dialysis against pure water. The completely dialyzed protein solution is frozen at a −70° C. freezer, and then lyophilized with a lyophilizer. The lyophilized powder is collected, which is the purified monoclonal antibody against total aflatoxin B1, B2, G1 and G2. The purified antibody can then be stored at −20° C. for future use.

In the above embodiment, the acetate buffer solution is prepared by mixing 0.29 gram (g) sodium acetate, 0.141 mL acetic acid, and water to a total volume of 100 mL. The 0.1 M phosphate buffer solution is prepared by mixing 0.8 g sodium chloride, 0.29 g sodium hydrogen phosphate dodecahydrate, 0.02 g potassium chloride and 0.02 g potassium dihydrogen phosphate and water to a total volume of 100 mL.

The present invention, among other things, has the following advantages:

(1) The hybridoma cell line 10G4 can be used to produce the monoclonal antibody against total aflatoxin B1, B2, G1 and G2. The titer of the 10G4 mouse ascites antibody measured through non-competitive ELISA can reach up to $5.12 \times 10^5$.

(2) The monoclonal antibody against total aflatoxin B1, B2, G1 and G2 can be used for better identification of aflatoxin B1, B2, G1 and G2 with good consistency. The 50% inhibitory concentrations ($IC_{50}$) for aflatoxin B1, B2, G1 and G2 are 2.09 nanogram (ng)/mL, 2.23 ng/mL, 2.19 ng/mL and 3.21 ng/mL respectively. The range of cross reacting rate for aflatoxin B1, B2, G1 and G2 is about 65.2%-100%.

(3) The monoclonal antibody against total aflatoxin B1, B2, G1 and G2 can be used for quantitative measurement of total aflatoxin B1, B2, G1 and G2.

DETAILED DESCRIPTION OF THE INVENTION

Example 1

Preparation of Hybridoma Cell Line 10G4

1. Animal Immunization

Six 6-week old BALB/c mice are immunized by the complete aflatoxin B1 antigen AFB1-BSA. The first immunization: emulsifying the complete aflatoxin B1 antigen and the equivalent amount of Freund's complete adjuvant, then multiple-point injecting the mice with the emulsion at the nape subcutaneously. The second immunization is performed after 4 weeks: emulsifying the complete aflatoxin B1 antigen and the equivalent amount of Freund's incomplete adjuvant, then injecting the mice with the emulsion intraperitoneally. The third immunization is performed 4 weeks after the second immunization, and the immunization method is the same as the second immunization. The fourth immunization is performed 3 weeks after the third immunization, and the immunization method is the same as the second immunization, i.e., intraperitoneal injection. The dose used for the 4 immunization processes can be the same, i.e., 50 μg for each mouse. For the first 3 immunizations, 8 days after each immunization, the blood is collected from the caudal vein, the serum is separated, and the mouse serum titer is monitored through indirect ELISA. 8 days after the fourth immunization, the blood is collected from the caudal vein, the serum is separated, the mouse serum titer is monitored through indirect ELISA method, and the serum sensitivity of the mice is monitored through indirect competitive ELISA. The mouse with relatively higher tilter and serum sensitivity than the other mice is chosen to perform the last booster immunization. Dose of the booster immunization is twice as those used in the previously immunization. The complete aflatoxin B1 antigen AFB1-BSA can be purchased from Sigma-Aldrich.

2. Cell Fusion

Three days after the final booster immunization, cell fusion is performed according to the common method using 50% (percentage by weight) polyethylene glycol (PEG, molecular weight: 1450) as fusion agent. The cell fusion is detailed as follows. The mouse is killed under aseptic conditions. Splenocytes are separated and mixed with mouse myeloma cells SP2/0 at a 5:1 ratio. The mixed cells are rinsed with RPMI-1640 media, and fused using the 50% PEG for 1 min. Then the container is filled with RPMI-1640 media. The solution is centrifuged and the supernatant is discarded. The fused cells of the splenocytes and mouse myeloma cells are re-suspended with 72 mL RPMI-1640 media. The re-suspended cells is pipetted into a 96-well cell culture plate (2 drops/well) and then cultured in a carbon dioxide incubator at 30° C. The RPMI-1640 media contains 20% (percentage by volume) of fetal calf serum, 2% (percentage by weight) of growth factor and 1% (percentage by weight) of hypoxanthine-aminopterin-thymidine (HAT). The above SP2/0 can be purchased from Shanghai Fankel Biological Technology Co., Ltd. The RPMI-1640 media can be purchase from Hyclone company. The HAT can be purchased from Sigma-Aldrich.

3. Selection and Cloning of Hybridoma Cells

After the cell fusion is kept for about 12 days, the cell colony grows to fill ½ of the well bottom and the culture solution becomes yellow, and antibody can be analyzed. The culture wells with hybridomas are selected through ELISA, which is performed in two steps: selecting positive wells which are against aflatoxin B1 rather than the carrier protein BSA through indirect ELISA; and testing the selected positive wells via step one through indirect competitive inhibition ELISA. The aflatoxin G2 can be used as competition antigen. Wells with high light absorption value and sensitivity (high light absorption value means that those wells with the competition source being 0, i.e., the positive control wells, have high measured values; high sensitivity means that those wells that has 50% inhibition rate, i.e., the $IC_{50}$ value, is low) are selected. Cloning is performed through limiting dilution method. After about 10 days from the cloning, the same two-step selection method is conducted. Repeat the selection and cloning 2-3 times, and the hybridoma cell line 10G4 is then obtained.

Example 2

Variable Region Sequencing for Hybridoma Cell Line 10G4 that Produced Monoclonal Antibody Against Total Aflatoxin B1, B2, G1 and G2

(1) Extracting total RNA: the total RNA extraction kit of Tiangen Biotech (Beijing) Co., Ltd is used and the total RNA of the hybridoma cell line 10G4 is extracted according to protocol of the kit.

(2) Synthesizing cDNA: the first chain of cDNA is synthesized by taking the total RNA obtained via Step (1) as template, the oligo$(dT)_{15}$ as primer, and performing the reverse transcription according to the SuperScript™-2 II Reverse Transcription protocol. The Primer oligo$(dT)_{15}$ is purchased from Invitrogen.

(3) Cloning variable region genes through PCR: a primer is designed according to the conserved sites of the mouse antibody gene sequence in GENEBANK, and the VL/VH region are amplified by taking cDNA as template. PCR procedure: 94° C. 30 seconds, 55° C. 1 min, 72° C. 1 min, 30 cycles of amplification, the last operation at 72° C. is prolonged to 10 min. The PCR product is separated by 1% (percentage by weight) agarose gel electrophoresis, and the DNA segments are purified. The purified DNA segment is inserted to the carrier pMD18-T and the inserted carrier pMD18-T is used to transform the *E. coli* DH5α competent cells. Positive colonies are selected and sent to Shanghai Sunny Biotechnology Co., Ltd for DNA sequencing. Sequences of the VH region primers are: 5'-AGG TSM ARC TGC AGS AGT CWG G-3' (22 mer) and 5'-TGA GGA GAC GGT GAC CGT GGT CCC TTG GCC CC-3' (32 mer), where S, M, R and W are degenerate bases, M=A/C, R=A/G, S=C/G and W=A/T. Sequences of the VL region primers are: 5'-GAC ATT GAG CTC ACC CAG CTT GGT GCC-3' (24 mer) and 5'-CCG TTT CAG CTC CAG CTT GGT CCC-3' (24 mer).

Obtained gene sequences: the length of the gene sequence encoding the VH region is 356 bp, see SEQ ID NO: 1 for the detailed sequence. According to the obtained gene sequence, the VH region encoded by this gene sequence has 118 amino acids, see SEQ ID NO: 3 for the detailed sequence. The length of the gene sequence encoding the VL region is 332 bp, see SEQ ID NO: 2 for the detailed sequence. According to the obtained gene sequence, the VL region encoded by this gene sequence has 110 amino acids, see SEQ ID NO:4 for the detailed sequence.

Example 3

Preparation, Purification, Subtype and Characteristic Assay of Monoclonal Antibody Against Total Aflatoxin B1, B2, G1 and G2

A BALB/c mouse is treated with Freund's incomplete adjuvant, and then is injected with the hybridoma cell line 10G4 obtained from Example 2 which can produce monoclonal antibody against total aflatoxin B1, B2, G1 and G2. The ascites of this mouse is collected and antibody is purified through the caprylic acid-ammonium sulfate (CA-AS) precipitation method detailed as follows. The mouse ascites is filtered with a piece of double-layer filter paper. The filtrate is centrifuged at 12000 r/min under 4° C. for more than 15 min. The supernatant is pipetted. The supernatant of the ascites is mixed with acetate buffer solution (4 times as much as the former). N-caprylic acid is added slowly while stirring. The volume of n-caprylic acid needed for each mL of ascites is about 33 μL. The mixture is kept at room temperature for 30~60 min and then stored at 4° C. for more than 2 h. The mixture is centrifuged at 12000 r/min under 4° C. for more than 30 min. The precipitate is discarded and the obtained supernatant is filtered with a piece of double-layer filter paper. Phosphate buffer solution (1/10 of the volume of the filtrate, mol concentration: 0.1 mol/L, pH value: 7.4) is added to the filtrate. The pH value of this mixture is adjusted to 7.4 using 2 mol/L sodium hydroxide solution and the pH adjusted mixture is precooled to 4° C. Ammonium sulfate is added slowly until the final concentration of ammonium sulfate reaches 0.277 g/mL in the solution. The solution is kept for more than 2 h at 4° C. and then centrifuged at 12000 r/min under 4° C. for more than 30 min. The supernatant is removed and the obtained precipitate is re-suspended with 0.01 mol/L phosphate buffer solution that is 1/10 of the volume of the original ascites. The re-suspended solution is put into a dialysis bag for dialysis against pure water. The completely dialyzed protein solution is frozen at −70° C. in a freezer, and then lyophilized with a lyophilizer. The lyophilized powder, i.e., the purified monoclonal antibody against total aflatoxin B1, B2, G1 and G2, is collected. The purified antibody is stored in a freezer at −20° C. for future use. The acetate buffer solution is prepared by adding 0.29 g of sodium acetate and 0.141 mL of acetic acid into water to a total volume of 100 mL. The 0.1 mol/L phosphate buffer solution is prepared by adding 0.8 g of sodium chloride, 0.29 g of sodium hydrogen phosphate dodecahydrate, 0.02 g of potassium chloride and 0.02 g of potassium dihydrogen phosphate into water to a total volume of 100 mL.

The subtype of the monoclonal antibody against total aflatoxin B1, B2, G1 and G2, which is secreted by the hybridoma cell line 10G4, is determined as IgG1 using subtype kit available on the market.

The titer of the mouse ascites antibodies of the 10G4 mouse is determined by non-competitive ELISA and the titer can reach up to $5.12\times10^5$. That is, the test result is positive even after the mouse ascites antibody has a $5.12\times10^5$-fold dilution. The sensitivity of the antibody against total aflatoxin B1, B2, G1 and G2, is determined according to indirect competitive inhibition ELISA. The 50% inhibitory concentrations ($IC_{50}$) are 2.09 ng/mL, 2.23 ng/mL, 2.19 ng/mL and 3.21 ng/mL respectively. The range of cross reacting rate for aflatoxin B1, B2, G1 and G2 is 65.2%-100%.

Example 4

Application of Monoclonal Antibody 10G4 Against Total Aflatoxin B1, B2, G1 and G2

4 standard curves are obtained according to Example 3 in respect to the result against aflatoxin B1, B2, G1 and G2. A new quantitative analysis curve for analyzing total aflatoxin of B1, B2, G1 and G2 is constructed by an averaging process of the 4 standard curves. The new curve is used to test total aflatoxin B1, B2, G1 and G2 of five sets of peanut samples. At the same time, a comparison analysis based on standard high performance GB/T 18979-2003 liquid chromatogram method is performed. The results from the above two methods shown high consistency. The detailed results are as follows:

Sample 1: total aflatoxin determined based on antibody 10G4 ELISA is 0.23 ng/mL; total aflatoxin determined by the high performance GB/T 18979-2003 liquid chromatogram method is 0.2 ng/mL;

Sample 2: total aflatoxin determined based on antibody 10G4 ELISA is 1.47 ng/mL; total aflatoxin determined by the high performance GB/T 18979-2003 liquid chromatogram method is 1.2 ng/mL;

Sample 3: total aflatoxin determined based on antibody 10G4 ELISA is 0.88 ng/mL; total aflatoxin determined by the high performance GB/T 18979-2003 liquid chromatogram method is 1.1 ng/mL;

Sample 4: total aflatoxin determined based on antibody 10G4 ELISA is negative; total aflatoxin determined by the high performance GB/T 18979-2003 liquid chromatogram method is negative;

Sample 5: total aflatoxin determined based on antibody 10G4 ELISA is 0.92 ng/mL; total aflatoxin determined by the high performance GB/T 18979-2003 liquid chromatogram method is 0.8 ng/mL.

What is claimed is:

1. A hybridoma cell line 10G4 deposited at the China Center for Type Culture Collection (CCTCC) with the CCTCC accession number of C201016.

2. A monoclonal antibody against total aflatoxin B1, B2, G1 and G2, wherein the monoclonal antibody is produced by hybridoma cell line 10G4 that is deposited at the China Center for Type Culture Collection (CCTCC) with the CCTCC accession number of C201016.

3. A method for producing the monoclonal antibody of claim 2, comprising:
   treating a BALB/c mouse by Freund's incomplete adjuvant;
   injecting the treated BALB/c mouse with hybridoma cell line 10G4;
   collecting ascites of the BALA/c mouse; and
   purifying the monoclonal antibody of claim 2 from the ascites.

* * * * *

SEQUENCE LISTING

```
<160> NUMBER OF SEQ ID NOS: 4

<210> SEQ ID NO 1
<211> LENGTH: 356
<212> TYPE: DNA
<213> ORGANISM: Mus musculus

<400> SEQUENCE: 1
aggtgcagct gcaggagtca gggggaggct tagtgaagcc tggagggtcc ctgaaactct      60
cctgtgcagc ctcaggattc actctcagta gtaatgacat gtcttgggtt cgccagacac     120
cggagaagag gctggagtgg gtcgcaagta ttagtagagg tggtaggtac acctactatc     180
cagacagtgt gaaggggcga ttcaccatct ccagagacaa agccaagaac acctgtatc      240 tgcaaatgaa cagtctgagg tctgaggata cggccatgta ttattgtgca agacactatg     300
gtagctactg gtacttcgat gtctgggggcc aagggaccac ggtcaccgtc tcctca        356

<210> SEQ ID NO 2
<211> LENGTH: 332
<212> TYPE: DNA
<213> ORGANISM: Mus musculus

<400> SEQUENCE: 2
ccgtttgatt tccagcttgg tgcccctcc gaacgtgtaa gctccctaat gtgctgacag        60
taataggttg cagcatcctc ctcctccaca ggatggatgt tgagggtgaa gtctgtccca     120
gacccactgc cactgaacct ggcagggacc ccagattcta ggttggatac aagatagatg     180
aggagtctgg gtggctgtcc tggtttctgt tggttccagt gcatataact atagccagat     240 gtactgcacac ttttgctggc cctgtatgag atggtggccc tctgcccag agatacagct     300 aaggaagctg gagactgggt gagctcaatg tc                                  332

<210> SEQ ID NO 3
<211> LENGTH: 118
<212> TYPE: PRT
<213> ORGANISM: Mus musculus

<400> SEQUENCE: 3

Val Gln Leu Gln Glu Ser Gly Gly Gly Leu Val Lys Pro Gly Gly Ser
 1               5                  10                  15

Leu Lys Leu Ser Cys Ala Ala Ser Gly Phe Thr Leu Ser Ser Asn Asp
                20                  25                  30

Met Ser Trp Val Arg Gln Thr Pro Glu Lys Arg Leu Glu Trp Val Ala
            35                  40                  45

Ser Ile Ser Arg Gly Gly Arg Tyr Thr Tyr Tyr Pro Asp Ser Val Lys
        50                  55                  60

Gly Arg Phe Thr Ile Ser Arg Asp Lys Ala Lys Asn Thr Leu Tyr Leu
```

```
                65                  70                  75                  80
Gln Met Asn Ser Leu Arg Ser Glu Asp Thr Ala Met Tyr Tyr Cys Ala
                85                  90                  95
Arg His Tyr Gly Ser Tyr Trp Tyr Phe Asp Val Trp Gly Gln Gly Thr
                100                 105                 110
Thr Val Thr Val Ser Ser
                115

<210> SEQ ID NO 4
<211> LENGTH: 110
<212> TYPE: PRT
<213> ORGANISM: Mus musculus

<400> SEQUENCE: 4

Asp Ile Glu Leu Thr Gln Ser Pro Ala Ser Leu Ala Val Ser Leu Gly
1               5                   10                  15
Gln Arg Ala Thr Ile Ser Tyr Arg Ala Ser Lys Ser Val Ser Thr Ser
                20                  25                  30
Gly Tyr Ser Tyr Met His Trp Asn Gln Gln Lys Pro Gly Gln Pro Pro
                35                  40                  45
Arg Leu Leu Ile Tyr Leu Val Ser Asn Leu Glu Ser Gly Val Pro Ala
                50                  55                  60
Arg Phe Ser Gly Ser Gly Ser Gly Thr Asp Phe Thr Leu Asn Ile His
65                  70                  75                  80
Pro Val Glu Glu Glu Asp Ala Ala Thr Tyr Tyr Cys Gln His Ile Arg
                85                  90                  95
Glu Leu Thr Arg Ser Glu Gly Ala Pro Ser Trp Lys Ser Asn
                100                 105                 110
```